US007632517B2

(12) United States Patent
Dugger, III et al.

(10) Patent No.: US 7,632,517 B2
(45) Date of Patent: *Dec. 15, 2009

(54) BUCCAL, POLAR AND NON-POLAR SPRAY CONTAINING ZOLPIDEM

(75) Inventors: Harry A. Dugger, III, Flemington, NJ (US); Mohammed Abd El-Shafy, Hauppauge, NY (US)

(73) Assignee: Novadel Pharma Inc., Flemington, NJ (US)

( * ) Notice: Subject to any disclaimer, the term of this patent is extended or adjusted under 35 U.S.C. 154(b) by 42 days.

This patent is subject to a terminal disclaimer.

(21) Appl. No.: 10/671,715

(22) Filed: Sep. 29, 2003

(65) Prior Publication Data

US 2004/0265239 A1 Dec. 30, 2004

Related U.S. Application Data

(63) Continuation-in-part of application No. 10/230,060, filed on Aug. 29, 2002, which is a continuation-in-part of application No. 09/537,118, filed on Mar. 29, 2000, which is a continuation-in-part of application No. PCT/US97/17899, filed on Oct. 1, 1997.

(51) Int. Cl.
A61K 9/08 (2006.01)
A61K 9/12 (2006.01)
A61M 11/00 (2006.01)

(52) U.S. Cl. .......................... 424/435; 424/45; 514/923

(58) Field of Classification Search ................. 424/435, 424/45; 514/923
See application file for complete search history.

(56) References Cited

U.S. PATENT DOCUMENTS

| 3,304,230 | A | 2/1967 | Abramson et al. ............. 167/82 |
| 3,784,684 | A | 1/1974 | Bossert et al. ................. 424/37 |
| 4,232,002 | A | 11/1980 | Nogrady ....................... 424/25 |
| 4,495,168 | A | 1/1985 | Schmolka |
| 4,689,233 | A | 8/1987 | Dvorsky et al. ............. 424/455 |
| 4,704,406 | A | 11/1987 | Stanislaus et al. |
| 4,755,389 | A | 7/1988 | Jones et al. ................. 424/456 |
| 4,814,161 | A | 3/1989 | Jinks et al. |
| 4,857,312 | A | 8/1989 | Hegasy et al. ................. 424/80 |
| 4,863,720 | A | 9/1989 | Burghart et al. |
| 4,863,970 | A | 9/1989 | Patel et al. |
| 4,919,919 | A | 4/1990 | Aouda et al. ................. 424/45 |
| 4,935,243 | A | 6/1990 | Borkan et al. ................ 424/441 |
| 5,011,678 | A | 4/1991 | Wang et al. ................... 424/45 |
| 5,047,230 | A | 9/1991 | Nagy et al. .................... 424/45 |
| 5,128,132 | A | 7/1992 | Parnell ..................... 424/195.1 |
| 5,135,753 | A | 8/1992 | Baker et al. ................. 424/435 |
| 5,143,731 | A | 9/1992 | Viegas et al. |
| 5,166,145 | A | 11/1992 | Jao et al. |
| 5,186,925 | A | 2/1993 | Cholcha ....................... 424/43 |
| 5,240,932 | A | 8/1993 | Morimoto et al. |
| 5,290,540 | A | 3/1994 | Prince et al. |
| 5,364,616 | A | 11/1994 | Singer et al. ................... 424/52 |
| 5,370,862 | A | 12/1994 | Klokkers-Bethke et al. ... 424/47 |
| 5,428,006 | A | 6/1995 | Bechgaard ..................... 424/45 |
| 5,456,677 | A | 10/1995 | Spector ....................... 604/290 |
| 5,457,100 | A | 10/1995 | Daniel ......................... 514/220 |
| 5,474,759 | A | 12/1995 | Fassberg et al. ................ 424/45 |
| 5,502,076 | A | 3/1996 | Dixit et al. |
| 5,519,059 | A | 5/1996 | Sawaya ....................... 514/599 |
| 5,593,684 | A | 1/1997 | Baker et al. .................. 208/252 |
| 5,602,182 | A | 2/1997 | Popli et al. |
| 5,605,674 | A | 2/1997 | Purewal et al. |
| 5,607,915 | A | 3/1997 | Patton |
| 5,635,161 | A | 6/1997 | Adjei et al. |
| 5,645,856 | A | 7/1997 | Lacy et al. |
| 5,719,197 | A | 2/1998 | Kanios et al. ............. 514/772.6 |
| 5,725,841 | A | 3/1998 | Duan et al. |
| 5,766,573 | A | 6/1998 | Purewal et al. ................. 424/45 |
| 5,795,909 | A | 8/1998 | Shashoua et al. |
| 5,824,307 | A | 10/1998 | Johnson |
| 5,869,082 | A | 2/1999 | Dugger, III .................. 424/435 |
| 5,891,465 | A | 4/1999 | Keller et al. |
| 5,906,811 | A | 5/1999 | Hersh |
| 5,908,611 | A | 6/1999 | Gottlieb et al. |
| 5,955,098 | A | 9/1999 | Dugger, III .................. 424/435 |
| 5,981,591 | A | 11/1999 | Deihl ......................... 514/568 |
| 6,071,539 | A | 6/2000 | Robinson et al. ............. 424/466 |
| 6,110,486 | A | 8/2000 | Dugger, III .................. 424/435 |
| 6,143,329 | A | 11/2000 | Kim |
| 6,212,227 | B1 | 4/2001 | Ko et al. |
| 6,258,032 | B1 | 7/2001 | Hammesfahr |
| 6,271,240 | B1 | 8/2001 | Simon |
| 6,299,900 | B1 | 10/2001 | Reed et al. |

(Continued)

FOREIGN PATENT DOCUMENTS

DE 3338978 5/1984

(Continued)

OTHER PUBLICATIONS

Cassidy, et al, Journal of Controlled R2/8/2007elaese, 25 (1993) 21-29, Controlled buccal delivery of buprenorphine.*

(Continued)

*Primary Examiner*—Mina Haghighatian
(74) *Attorney, Agent, or Firm*—Dickstein Shapiro LLP

(57) ABSTRACT

Buccal aerosol sprays or capsules using polar and non-polar solvents have now been developed which provide zolpidem for rapid absorption through the oral mucosa, resulting in fast onset of effect. The buccal polar compositions of the invention comprise formulation I: aqueous polar solvent, zolpidem, and optional flavoring agent; formulation II: aqueous polar solvent, zolpidem, optionally flavoring agent, and propellant; formulation III: non-polar solvent, zolpidem, and optional flavoring agent; formulation IV: non-polar solvent, zolpidem, optional flavoring agent, and propellant; formulation V: a mixture of a polar solvent and a non-polar solvent, zolpidem, and optional flavoring agent; formulation VI: a mixture of a polar solvent and a non-polar solvent, zolpidem, optional flavoring agent, and propellant.

21 Claims, 1 Drawing Sheet

U.S. PATENT DOCUMENTS

| | | | |
|---|---|---|---|
| 6,375,975 | B1 | 4/2002 | Modi |
| 6,458,842 | B1 | 10/2002 | Dickinson et al. |
| 6,512,002 | B2 | 1/2003 | Lee et al. |
| 6,676,931 | B2 | 1/2004 | Dugger |
| 6,706,255 | B2 | 3/2004 | Dickinson et al. |
| 6,816,452 | B1 | 11/2004 | Machata |
| 6,969,508 | B2 | 11/2005 | Dugger, III |
| 6,977,070 | B2 | 12/2005 | Dugger, III |
| 6,998,110 | B2 | 2/2006 | Dugger, III |
| 7,202,233 | B2 | 4/2007 | Penkler |
| 2003/0077227 | A1 | 4/2003 | Dugger |
| 2003/0082107 | A1 | 5/2003 | Dugger |
| 2004/0136913 | A1 | 7/2004 | Adb El-Shafy et al. |
| 2004/0141923 | A1 | 7/2004 | Dugger et al. |
| 2006/0222597 | A1 | 10/2006 | Dugger et al. |
| 2007/0048229 | A1 | 3/2007 | Dugger et al. |

FOREIGN PATENT DOCUMENTS

| | | |
|---|---|---|
| DE | 3246081 | 6/1984 |
| DE | 4007705 | 9/1991 |
| DE | 4038203 | 6/1992 |
| DE | 4112303 | 10/1992 |
| DE | 4132176 | 4/1993 |
| EP | 0140434 | 5/1985 |
| EP | 0213 108 | 3/1987 |
| EP | 0315960 | 5/1989 |
| EP | 0386700 | 9/1990 |
| EP | 0471161 | 2/1992 |
| EP | 0504112 | 9/1992 |
| EP | 0605483 | 4/1993 |
| EP | 0557129 | 8/1993 |
| EP | 0656206 | 6/1995 |
| EP | 0719549 | 7/1996 |
| EP | 1029536 | 8/2000 |
| FR | 2633933 | 1/1990 |
| GB | 2082457 | 3/1982 |
| GB | 2295318 | 5/1996 |
| IE | 912509 AI | 2/1992 |
| JP | 02-026661 * | 1/1990 |
| WO | WO 90/01046 | 2/1990 |
| WO | WO 93/03751 | 3/1993 |
| WO | WO93/04671 | 3/1993 |
| WO | WO 94/10987 | 5/1994 |
| WO | WO94/13280 | 6/1994 |
| WO | WO95/24893 | 9/1995 |
| WO | WO 95/31217 | 11/1995 |
| WO | WO 97/38662 | 10/1997 |
| WO | WO 97/38663 | 10/1997 |
| WO | WO 97/38687 | 10/1997 |
| WO | WO 98/29097 | 7/1998 |
| WO | WO 98/52540 | 11/1998 |
| WO | WO 98/52545 | 11/1998 |
| WO | WO 99/16417 | 4/1999 |
| WO | WO 00/06534 | 2/2000 |
| WO | WO 00/27359 | 5/2000 |
| WO | WO 00/62757 | 10/2000 |
| WO | WO 01/66089 | 9/2001 |
| WO | WO 02/43695 | 6/2002 |
| WO | WO 02/066089 | 8/2002 |
| WO | WO 02/094232 | 11/2002 |
| WO | WO 02/094234 | 11/2002 |

OTHER PUBLICATIONS

Physician's Desk Reference, 49$^{th}$ Edition, 1995, p. 2304-2306.*
*Goodman and Gilman's The Pharmacological Basis of Therapeutics*, 9th ed., pp. 490.
*Goodman and Gilman's The Pharmacological Basis of Therapeutics*, 9th ed., pp. 496.
*Goodman and Gilman's The Pharmacological Basis of Therapeutics*, 9th ed., pp. 497.
*Goodman and Gilman's The Pharmacological Basis of Therapeutics*, 9th ed., pp. 471-472.
*Drug Facts and Comparisons* (Jan. 2002) pp. 186c-186d.
*Goodman and Gilman's The Pharmacological Basis of Therapeutics*, 9th ed., (1996), pp. 141-154, 169-170, 260, 303-304, 324, 362, 372, 420-422, 427, 471, 472, 478-480, 484, 490, 496-497, 928-930.
Karlsson, et al.; "A Comparison of the Effect of Inhaled Diuretics on Airway Reflexes in Humans and Guinea Pigs", *The American Physiological Society*, pp. 434-438 (1992).
L.W. Brox, et al., "Studies on the Growth Inhibition and Metabolism of 2'-Deoxy-2' fluorocytidine in Cultured Human Lymphoblasts"; *Cancer Research*, vol. 34, pp. 1838-1842 (1974).
Maarek et al., "The Safety and Efficacy of Zolpidem in Insomniac Patients: a Long-Term Open Study in General Practice," J. Int. Med. Res., 1992, 2092), 162-170.
Mochizuki, et al.; Inhaled Diuretics Attenuate Acid-Induced Cough in Children With Asthma; Chest, 107/2 pp. 413-417 (1995).
Physician's Desk Reference, 1995, pp. 858-861, 2436-2441, 2548-2550.
Schlich, D., et al., "Long-term treatment of insomnia with zolpidem: a multicentre general practitioner study of 107 patients." The Journal of International Medical Research, 1991, 19(3), pp. 271-279.
Ting-Chao Chou, et al.; "Pharmacological Disposition and Metabolic Fate of 2'-Fluoro-5-iodo-1-β-D-arabinofuranosylcytosine in Mice and Rats"; Cancer Research, vol. 41, pp. 3336-3342 (1981).
Woodley et al., Manual of Medical Therapeutics, 27th Edition, 1992, pp. 341 and 370-371.
Written Opinion of the International Searching Authority—Feb. 28, 2006.
Ye, Jiang Hong et al.; "Ondansetron Exhibits The Properties of a Local Anesthetic"; Anesthesia and Analgesia, vol. 85. No. 5, Nov. 1997; pp. 1116-1121.
Zervakis, et al.; "Taste Effects of Lingual Application of Cardiovascular Medications"; Physiology & Behavior, 68: pp. 405-413 (2000).
Cosdon, Christina K., "Sprays sold as better way to get vitamins," *Seminole Times; Seminole Business Digest*, Nov. 6, 1996.
Shojaei, Amir H., "Buccal Mucosa as a Route for Systemic Drug Delivery: A Review", *J Pharm Pharmaceut Sci*, 1(1):15-30, 1998.

* cited by examiner

BUCCAL, POLAR AND NON-POLAR SPRAY CONTAINING ZOLPIDEM

CROSS REFERENCE TO RELATED APPLICATIONS

This application is a continuation-in-part of application Ser. No. 10/230,060, filed Aug. 29, 2002, pending, which is a continuation-in-part of application Ser. No. 09/537,118, filed Mar. 29, 2000 which is a continuation-in-part of the U.S. national phase designation of PCT/US97/17899 filed Oct. 1, 1997, the disclosures of which are incorporated by reference herein in their entirety.

BACKGROUND OF THE INVENTION

It is known that certain biologically active compounds are better absorbed through the oral mucosa than through other routes of administration, such as through the stomach or intestine. However, formulations suitable for such administration by these latter routes present their own problems. For example, the biologically active compound must be compatible with the other components of the composition such as propellants, solvents, etc. Many such formulations have been proposed. For example, U.S. Pat. No. 4,689,233, Dvorsky et al., describes a soft gelatin capsule for the administration of the anti-coronary drug nifedipine dissolved in a mixture of polyether alcohols. U.S. Pat. No. 4,755,389, Jones et al., describes a hard gelatin chewable capsule containing nifedipine. A chewable gelatin capsule containing a solution or dispersion of a drug is described in U.S. Pat. No. 4,935,243, Borkan et al. U.S. Pat. No. 4,919,919, Aouda et al, and U.S. Pat. No. 5,370,862, Klokkers-Bethke, describe a nitroglycerin spray for administration to the oral mucosa comprising nitroglycerin, ethanol, and other components. An orally administered pump spray is described by Cholcha in U.S. Pat. No. 5,186,925. Aerosol compositions containing a hydrocarbon propellant and a drug for administration to a mucosal surface are described in U.K. 2,082,457, Su, U.S. Pat. No. 3,155,574, Silson et al., U.S. Pat. No. 5,011,678, Wang et al., and by Parnell in U.S. Pat. No. 5,128,132. It should be noted that these references discuss bioavailability of solutions by inhalation rather than through the membranes to which they are administered.

Zolpidem is a imidazopyridine having the structure shown below:

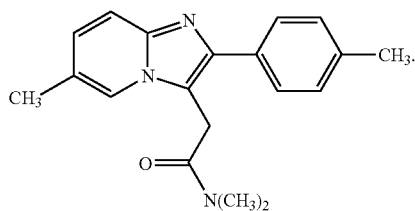

The chemical name for zolpidem is N,N, 6-trimethyl-2-p-tolyl-imidazo[1,2-a]pyridine-3-acetamide Zolpidem is a non-benzodiazepine sedative-hypnotic and is used to treat insomnia. To treat insomnia, zolpidem is typically administered orally at a dose of between 10 and 25 mg. Typically zolpidem is administered as the tartrate salt, i.e., N,N, 6-trimethyl-2-p-tolyl-imidazo[1,2-a]pyridine-3-acetamide L-(+)-tartrate (2:1). Following discontinuation of zolpidem the beneficial effects on sleep can last for up to a week. Tolerance and physical dependence is only rarely observed with zolpidem. (*Goodman and Gilman's The Pharmacological Basis of Therapeutics*, 9$^{th}$ ed., pp. 471-472).

SUMMARY OF THE INVENTION

A buccal aerosol spray or soft bite gelatin capsule using a polar or non-polar solvent has now been developed which provides biologically active compounds for rapid absorption through the oral mucosa, resulting in fast onset of effect.

The buccal aerosol spray compositions of the present invention, for transmucosal administration of a pharmacologically active compound soluble in a pharmacologically acceptable non-polar solvent comprise in weight % of total composition: pharmaceutically acceptable propellant 5-80%, nonpolar solvent 19-85%, active compound 0.05-50%, suitably additionally comprising, by weight of total composition a flavoring agent 0.01-10%. Preferably the composition comprises: propellant 10-70%, non-polar solvent 25-89.9%, active compound 0.01-40%, flavoring agent 1-8%; most suitably propellant 20-70%, non-polar solvent 25-74.75%, active compound 0.25-35%, flavoring agent 2-7.5%.

The buccal polar aerosol spray compositions of the present invention, for transmucosal administration of a pharmacologically active compound soluble in a pharmacologically acceptable polar solvent are also administrable in aerosol form driven by a propellant. In this case, the composition comprises in weight % of total composition: aqueous polar solvent 10-97%, active compound 0.1-25%, suitably additionally comprising, by weight of total composition a flavoring agent 0.05-10% and propellant: 2-10%. Preferably the composition comprises: polar solvent 20-97%, active compound 0.1-15%, flavoring agent 0.1-5% and propellant 2-5%; most suitably polar solvent 25-97%, active compound 0.2-25%, flavoring agent 0.1-2.5% and propellant 2-4%.

In another embodiment, the buccal polar aerosol spray compositions of the present invention for transmucosal administration of a pharmacologically active compound (i.e., those administrable in aerosol form driven by a propellant) comprises a mixture of a polar solvent and a non-polar solvent comprising in weight % of total composition: solvent 10-97%, active compound 0.05-50%, propellant 5-80%, and optionally a taste mask and/or flavoring agent 0.01-10%. Preferably the composition comprises: solvent 20-97%, active compound 0.1-40%, propellant 10-70%, and taste mask and/or flavoring agent 1-8%; most suitably solvent 25-97%, active compound 0.25-35%, propellant 20-70%, and taste mask and/or flavoring agent 2-7.5%. The ratio of the polar solvent to the non-polar solvent can range from about 1:99 to about 99:1, preferable from about 60:40 to about 40:60, and more preferably about 50:50.

The buccal pump spray composition of the present invention, i.e., the propellant free composition, for transmucosal administration of a pharmacologically active compound wherein said active compound is soluble in a pharmacologically acceptable non-polar solvent comprises in weight % of total composition: non-polar solvent 30-99.69%, active compound 0.005-55%, and suitably additionally, flavoring agent 0.1-10%.

The buccal polar pump spray compositions of the present invention, i.e., the propellant free composition, for transmucosal administration of a pharmacologically active compound soluble in a pharmacologically acceptable polar solvent comprises in weight % of total composition: aqueous polar solvent 30-99.69%, active compound 0.001-60%, suitably additionally comprising, by weight of total composition a flavoring agent 0.1-10%. Preferably the composition comprises: polar solvent 37-98.58%, active compound 0.005-55%, flavoring agent 0.5-8%; most suitably polar solvent 60.9-97.06%, active compound 0.01-40%, flavoring agent 0.75-7.5%.

In another embodiment, the buccal pump spray composition (i.e., the propellant free composition) for transmucosal administration of a pharmacologically active compound comprises a mixture of a polar solvent and a non-polar solvent comprising in weight % of total composition solvent 30-99.69%, active compound 0.001-60%, and optionally a taste mask and/or flavoring agent 0.1-10%. Preferably the composition comprises: solvent 37-98.58%, active compound 0.005-55%, taste mask and/or flavoring agent 0.5-8%; more preferably the composition comprises solvent 60.9-97.06%, active compound 0.01-40%, and taste mask and/or flavoring agent 0.75-7.5%. The ratio of the polar solvent to the non-polar solvent can range from about 1:99 to about 99:1, preferable about 60:40 to about 40:60, and more preferably about 50:50.

The soft bite gelatin capsules of the present invention for transmucosal administration of a pharmacologically active compound, at least partially soluble in a pharmacologically acceptable non-polar solvent, having charged thereto a fill composition comprise in weight % of total composition: non-polar solvent 4-99.99%, emulsifier 0-20%, active compound 0.01-80%, provided that said fill composition contains less than 10% of water, suitably additionally comprising, by weight of the composition: flavoring agent 0.01-10%. Preferably, the soft bite gelatin capsule comprises: non-polar solvent 21.5-99.975%, emulsifier 0-15%, active compound 0.025-70%, flavoring agent 1-8%; most suitably: nonpolar solvent 28.5-97.9%, emulsifier 0-10%, active compound 0.1-65.0%, flavoring agent 2-6%.

The soft bite polar gelatin capsules of the present invention for transmucosal administration of a pharmacologically active compound, at least partially soluble in a pharmacologically acceptable polar solvent, having charged thereto a composition comprising in weight % of total composition: polar solvent 25-99.89%, emulsifier 0-20%, active compound 0.01-65%, provided that said composition contains less than 10% of water, suitably additionally comprising, by weight of the composition: flavoring agent 01-10%. Preferably, the soft bite gelatin capsule comprises: polar solvent 37-99.95%, emulsifier 0-15%, active compound 0.025-55%, flavoring agent 1-8%; most suitably: polar solvent 44-96.925%, emulsifier 0-10%, active compound 0.075-50%, flavoring agent 2-6%.

It is an object of the invention to coat the mucosal membranes either with fine droplets of spray containing the active compounds or a solution or paste thereof from bite capsules.

It is also an object of the invention to administer to the oral mucosa of a mammalian in need of same, preferably man, by spray or bite capsule, a predetermined amount of a biologically active compound by this method or from a soft gelatin capsule.

A further object is a sealed aerosol spray container containing a composition of the non polar or polar aerosol spray formulation, and a metered valve suitable for releasing from said container a predetermined amount of said composition.

As the propellant evaporates after activation of the aerosol valve, a mist of fine droplets is formed which contains solvent and active compound.

The propellant is a non-Freon material, preferably a $C_{3-8}$ hydrocarbon of a linear or branched configuration. The propellant should be substantially non-aqueous. The propellant produces a pressure in the aerosol container such that under expected normal usage it will produce sufficient pressure to expel the solvent from the container when the valve is activated but not excessive pressure such as to damage the container or valve seals.

The non-polar solvent is a non-polar hydrocarbon, preferably a $C_{7-18}$ hydrocarbon of a linear or branched configuration, fatty acid esters, and triglycerides such as miglyol. The solvent must dissolve the active compound and be miscible with the propellant, i.e., solvent and propellant must form a single phase at a temperature of 0-40° C. a pressure range of between 1-3 atm.

The polar and non-polar aerosol spray compositions of the invention are intended to be administered from a sealed, pressurized container. Unlike a pump spray, which allows the entry of air into the container after every activation, the aerosol container of the invention is sealed at the time of manufacture. The contents of the container are released by activation of a metered valve, which does not allow entry of atmospheric gasses with each activation. Such containers are commercially available.

A further object is a pump spray container containing a composition of the pump spray formulation, and a metered valve suitable for releasing from said container a predetermined amount of said composition.

A further object is a soft gelatin bite capsule containing a composition of as set forth above. The formulation may be in the form of a viscous solution or paste containing the active compounds. Although solutions are preferred, paste fills may also be used where the active compound is not soluble or only partially soluble in the solvent of choice. Where water is used to form part of the paste composition, it should not exceed 10% thereof. (All percentages herein are by weight unless otherwise indicated.)

The polar or non-polar solvent is chosen such that it is compatible with the gelatin shell and the active compound. The solvent preferably dissolves the active compound. However, other components wherein the active compound is not soluble or only slightly soluble may be used and will form a paste fill.

Soft gelatin capsules are well known in the art. See, for example, U.S. Pat. No. 4,935,243, Borkan et al., for its teaching of such capsules. The capsules of the present invention are intended to be bitten into to release the low viscosity solution or paste therein, which will then coat the buccal mucosa with the active compounds. Typical capsules, which are swallowed whole or bitten and then swallowed, deliver the active compounds to the stomach, which results in significant lag time before maximum blood levels can be achieved or subject the compound to a large first pass effect. Because of the enhanced absorption of the compounds through the oral mucosa and no chance of a first pass effect, use of the bite capsules of the invention will eliminate much of the lag time, resulting in hastened onset of biological effect. The shell of a soft gelatin capsule of the invention may comprise, for example: gelatin: 50-75%, glycerin 20-30%, colorants 0.5-1.5%, water 5-10%, and sorbitol 2-10%.

The active compound may include, biologically active peptides, central nervous system active amines, sulfonyl ureas, antibiotics, antifungals, antivirals, sleep inducers, antiasthmatics, bronchial dilators, antiemetics, histamine H-2 receptor antagonists, barbiturates, prostaglandins and neutraceuticals.

The active compounds may also include antihistamines, alkaloids, hormones, benzodiazepines and narcotic analgesics. While not limited thereto, these active compounds are particularly suitable for non-polar pump spray formulation and application.

The active compounds may also include p-FOX (fatty acid oxidation) inhibitors, acetylcholinesterase inhibitors, nerve impulse inhibitors, anti-cholinergics, anti-convulsants, anti-psychotics, anxiolytic agents, dopamine metabolism inhibitors, agents to treat post stroke sequelae, neuroprotectants, agents to treat Alzheimer's disease, neurotransmitters, neurotransmitter agonists, sedatives, agents for treating attention deficit disorder, agents for treating narcolepsy, central adregenic antagonists, anti-depression agents, agents for treating Parkinson's disease, benzodiazepine antagonists, stimulants, neurotransmitter antagonists, tranquilizers, or a mixture thereof.

In one embodiment, the active compound is zolpidem or a pharmaceutically acceptable salt thereof.

DESCRIPTION OF THE PREFERRED EMBODIMENTS

Figure 1:
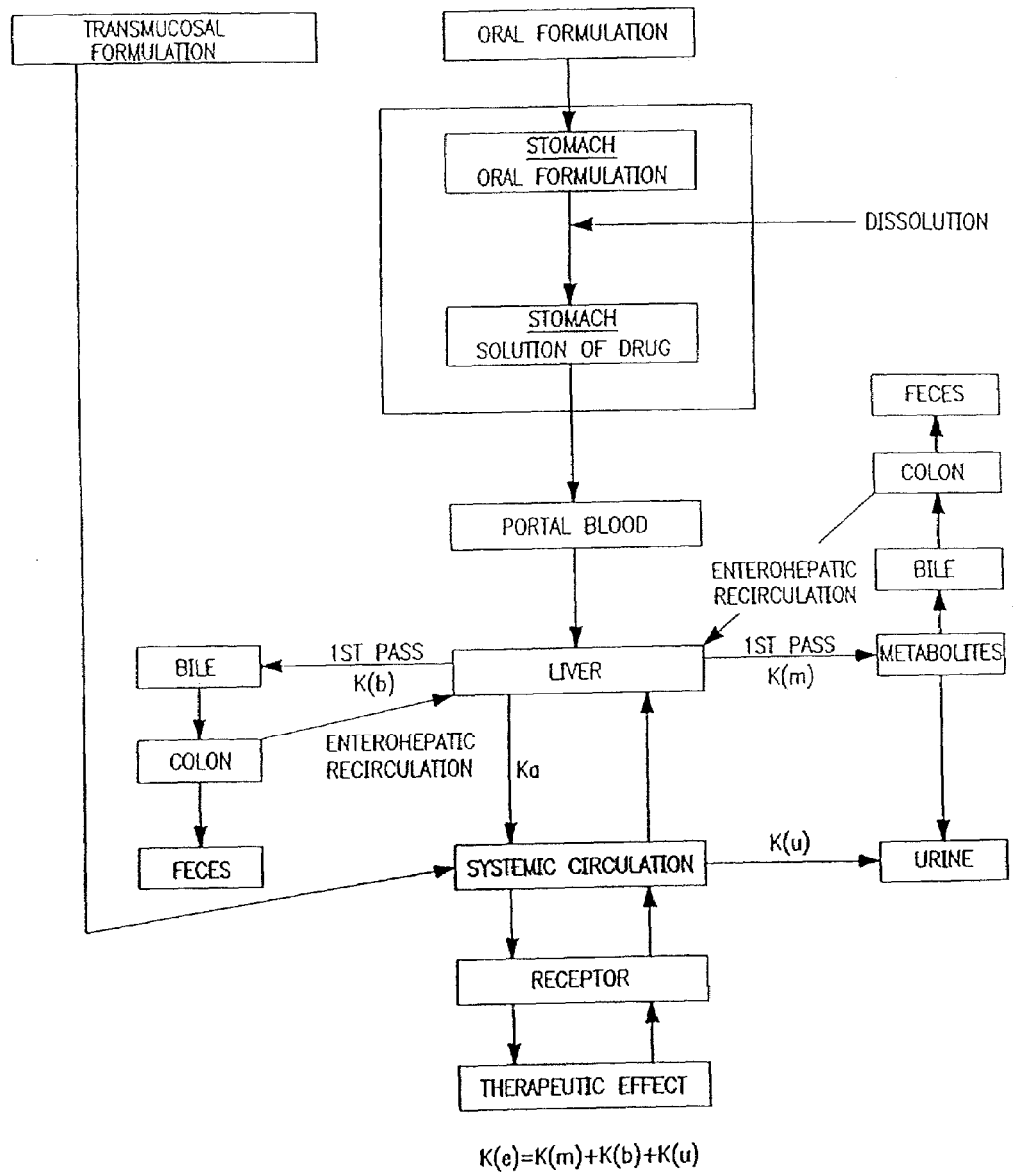
FIG. 1. is a schematic diagram showing routes of absorption and processing of pharmacologically active substances in a mammalian system.

The preferred active compounds of the present invention are in an ionized, salt form or as the free base of the pharmaceutically acceptable salts thereof (provided, for the aerosol or pump spray compositions, they are soluble in the spray solvent). These compounds are soluble in the non-polar solvents of the invention at useful concentrations or can be prepared as pastes at useful concentrations. These concentrations may be less than the standard accepted dose for these compounds since there is enhanced absorption of the compounds through the oral mucosa. This aspect of the invention is especially important when there is a large (40-99.99%) first pass effect.

As propellants for the non polar sprays, propane, N-butane, iso-butane, N-pentane, iso-pentane, and neo-pentane, and mixtures thereof may be used. N-butane and iso-butane, as single gases, are the preferred propellants. It is permissible for the propellant to have a water content of no more than 0.2%, typically 0.1-0.2%. All percentages herein are by weight unless otherwise indicated. It is also preferable that the propellant be synthetically produced to minimize the presence of contaminants which are harmful to the active compounds. These contaminants include oxidizing agents, reducing agents, Lewis acids or bases, and water. The concentration of each of these should be less than 0.1%, except that water may be as high as 0.2%.

Suitable non-polar solvents for the capsules and the non-polar sprays include ($C_2$-$C_{24}$) fatty acid ($C_2$-$C_6$) esters, $C_7$-$C_{18}$ hydrocarbon, $C_2$-$C_6$ alkanoyl esters, and the triglycerides of the corresponding acids. When the capsule fill is a paste, other liquid components may be used instead of the above low molecular weight solvents. These include soya oil, corn oil, other vegetable oils.

As solvents for the polar capsules or sprays there may be used low molecular weight polyethyleneglycols (PEG) of 400-1000 Mw (preferably 400-600), low molecular weight ($C_2$-$C_8$) mono and polyols and alcohols of $C_7$-$C_{18}$ linear or branch chain hydrocarbons, glycerin may also be present and water may also be used in the sprays, but only in limited amount in the capsules.

It is expected that some glycerin and water used to make the gelatin shell will migrate from the shell to the fill during the curing of the shell. Likewise, there may be some migration of components from the fill to the shell during curing and even throughout the shelf-life of the capsule.

Therefore, the values given herein are for the compositions as prepared, it being within the scope of the invention that minor variations will occur.

The preferred flavoring agents are synthetic or natural oil of peppermint, oil of spearmint, citrus oil, fruit flavors, sweeteners (sugars, aspartame, saccharin, etc.), and combinations thereof.

The compositions may further include a taste mask. The term "taste mask" as used herein means an agent that can hide or minimize an undesirable flavor such as a bitter or sour flavor. A representative taste mask is a combination of vanillin, ethyl vanillin, maltol, iso-amyl acetate, ethyl oxyhydrate, anisic aldehyde, and propylene glycol (commercially available as "PFC 9885 Bitter Mask" from Pharmaceutical Flavor Clinic of Camden, N.J.). A taste mask in combination with a flavoring agent is particularly advantageous when the active compound is an alkaloid since alkaloids often have a bitter taste.

The active substances include the active compounds selected from the group consisting of cyclosporine, sermorelin, octreotide acetate, calcitonin-salmon, insulin lispro, sumatriptan succinate, clozepine, cyclobenzaprine, dexfenfluramine hydrochloride, glyburide, zidovudine, erythromycin, ciprofloxacin, ondansetron hydrochloride, dimenhydrinate, cimetidine hydrochloride, famotidine, phenyloin sodium, phenyloin, carboprost thromethamine, carboprost, diphenhydramine hydrochloride, isoproterenol hydrochloride, terbutaline sulfate, terbutaline, theophylline, albuterol sulfate and neutraceuticals, that is to say nutrients with pharmacological action such as but not limited to camitine, valerian, echinacea, and the like.

In another embodiment, the active compound is a p-FOX (fatty acid oxidation) inhibitor, acetylcholinesterase inhibitor, nerve impulse inhibitor, anti-cholinergic, anti-convulsant, anti-psychotic, anxiolytic agent, dopamine metabolism inhibitor, agent to treat post stroke sequelae, neuroprotectant, agent to treat Alzheimer's disease, neurotransmitter, neurotransmitter agonist, sedative, agent for treating attention deficit disorder, agent for treating narcolepsy, central adregenic antagonist, anti-depression agent, agent for treating Parkinson's disease, benzodiazepine antagonist, stimulant, neurotransmitter antagonist, tranquilizer, or a mixture thereof.

In one embodiment the active compound is a p-FOX inhibitor. A suitable p-FOX inhibitor for use in the buccal sprays of the invention includes, but is not limited to, ranolazine.

In one embodiment the active compound is an acetylcholinesterase inhibitor. Suitable acetylcholinesterase inhibitors for use in the buccal sprays of the invention include, but are not limited to, galantamine, neostigmine, physostigmine, and edrophonium.

In one embodiment the active compound is a nerve impulse inhibitor. Suitable nerve impulse inhibitors for use in the buccal sprays of the invention include, but are not limited to, levobupivacaine, lidocaine, prilocalne, mepivacaine, propofol, rapacuronium bromide, ropivacaine, tubocurarine, atracurium, doxaurium, mivacurium, pancuronium, vercuronium, pipecuronium, and rocuronium.

In one embodiment the active compound is an anti-cholinergic. Suitable anti-cholinergics for use in the buccal sprays of the invention include, but are not limited to, amantadine, ipratropium, oxitropium, and dicycloverine.

In one embodiment the active compound is an anti-convulsant. Suitable anti-convulsants for use in the buccal sprays of the invention include, but are not limited to, acetazolamide, carbamazepine, clonazepam, diazepam, divalproex (valproic acid), ethosuximide, lamotrignine acid, levetriacetam, oxcarbazepine, phenobarbital, phenyloin, pregabalin, primidone, remacemide, trimethadione, topiramate, vigabatrin, and zonisamide.

In one embodiment the active compound is an anti-psychotic. Suitable anti-psychotics for use in the buccal sprays of the invention include, but are not limited to, amisulpride, aripiprazole bifemelane, bromperidol, clozapine, chlorpromazine, haloperidol, iloperidone loperidone, olanzapine, quetiapine, fluphenazine, fumarate, risperidone, thiothixene, thioridazine, sulpride, and ziprasidone, In one embodiment the active compound is an anxiolytic agent. Suitable anxiolytic agents for use in the buccal sprays of the invention include, but are not limited to, amitryptiline, atracurium, buspirone, chlorzoxazone, clorazepate, cisatracurium, cyclobenzaprine, eperisone, esopiclone, hydroxyzine, mirtazapine, mivacurium, pagoclone, sulperide, zaleplon, and zopiclone.

In one embodiment the active compound is a dopamine metabolism inhibitor. Suitable dopamine metabolism inhibitors for use in the buccal sprays of the invention include, but are not limited to, entacapone, lazebemide, selegiline, and tolcapone.

In one embodiment the active compound is an agent to treat post stroke sequelae. Suitable agents to treat post stroke sequelae for use in the buccal sprays of the invention include, but are not limited to, glatiramer, interferon beta 1A, interferon beta 1B, estradiol, and progesterone.

In one embodiment the active compound is a neuroprotectant. Suitable neuroprotectants for use in the buccal sprays of the invention include, but are not limited to, donepezil, memanine, nimodipine, riluzole, rivastigmine, tacrine, TAK147, and xaliproden.

In one embodiment the active compound is an agent to treat Alzheimer's disease. Suitable agents to treat Alzheimer's disease for use in the buccal sprays of the invention include, but are not limited to, carbidopa, levodopa, tacrine, donezepil, rivastigmine, and galantamine.

In one embodiment the active compound is a neurotransmitter. Suitable neurotransmitters for use in the buccal sprays of the invention include, but are not limited to, acetylcholine, serotonin, 5-hydroxytryptamine (5-HT), GABA, glutamate, aspartate, glycine, histamine, epinephrine, norpinephrine, dopamine, adenosine, ATP, and nitric oxide.

In one embodiment the active compound is a neurotransmitter agonist. Suitable neurotransmitter agonists for use in the buccal sprays of the invention include, but are not limited to, almotriptan, aniracetam, atomoxetine, benserazide, bromocriptine, bupropion, cabergoline, citalopram, clomipramine, desipramine, diazepam, dihydroergotamine, doxepin duloxetine, eletriptan, escitalopram, fluvoxamine, gabapentin, imipramine, moclobemide, naratriptan, nefazodone, nefiracetam acamprosate, nicergoline, nortryptiline, paroxetine, pergolide, pramipexole, rizatriptan, ropinirole, sertraline, sibutramine, sumatriptan, tiagabine, trazodone, venlafaxine, and zolmitriptan.

In one embodiment the active compound is a sedative. Suitable sedatives for use in the buccal sprays of the invention include, but are not limited to, dexmedetomidine, eszopiclone, indiplon, zolpidem, and zaleplon.

In one embodiment the active compound is an agent for treating attention deficit disorder. Suitable agents for treating attention deficit disorder for use in the buccal sprays of the invention include, but are not limited to, amphetamine, dextroamphetamine, methylphenidate, and pemoline.

In one embodiment the active compound is an agent for treating narcolepsy. Suitable agents for treating narcolepsy for use in the buccal sprays of the invention include, but are not limited to, modafinil and mazindol.

In one embodiment the active compound is a central adregenic antagonists. A suitable central adregenic antagonists for use in the buccal sprays of the invention includes, but is not limited to, mesoridazine.

In one embodiment the active compound is an anti-depression agent. Suitable anti-depression agents for use in the buccal sprays of the invention include, but are not limited to, amitriptyline, amoxapine, bupropion, clomipramine, clomipramine, clorgyline, desipramine, doxepin, fluoxetine, imipramine, isocarboxazid, maprotiline, mirtazapine, nefazodone, nortriptyline, paroxetine, phenelzine, protriptyline, sertraline, tranylcypromine, trazodone, and venlafaxine.

In one embodiment the active compound is an agent for treating Parkinson's disease. Suitable agents for treating Parkinson's disease for use in the buccal sprays of the invention include, but are not limited to, amantadine, bromocriptine, carvidopa, levodopa, pergolide, and selegiline.

In one embodiment the active compound is a benzodiazepine antagonist. A suitable benzodiazepine antagonist for use in the buccal sprays of the invention includes, but is not limited to, flumazenil.

In one embodiment the active compound is a neurotransmitter antagonist. A suitable neurotransmitter antagonist for use in the buccal sprays of the invention includes, but is not limited, to deramciclane.

In one embodiment the active compound is a stimulant. Suitable stimulants for use in the buccal sprays of the invention include, but are not limited to, amphetamine, dextroamphetamine, dinoprostone, methylphenidate, methylphenidate, modafinil, and pemoline.

In one embodiment the active compound is a tranquilizer. A suitable tranquilizer for use in the buccal sprays of the invention includes, but is not limited to, mesoridazine.

In a another embodiment, the active compound is zolpidem or a pharmaceutically acceptable salt thereof. In one embodiment, the active compound is zolpidem tartrate.

Typically, when zolpidem or a pharmaceutically acceptable salt thereof is the active compound the buccal spray contains from about 0.01 to 20 weight/weight (w/w) percent zolpidem, more preferably 0.1 to 15 w/w percent zolpidem, and most preferably 0.2 to 10 w/w percent zolpidem.

The invention further relates to a method of treating insomnia in a patient by spraying the oral mucosa of the patient with a therapeutically effective amount of a buccal spray comprising zolpidem or a pharmaceutically acceptable salt thereof.

The formulations of the present invention comprise an active compound or a pharmaceutically acceptable salt thereof. The term "pharmaceutically acceptable salts" refers to salts prepared from pharmaceutically acceptable non-toxic acids or bases including organic and inorganic acids or bases.

When an active compound of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methyl-glucosamine, morpholine, piperazine, piperidine, polyamine resins, procaine, purine, theobromine, triethylamine, trimethylamine, tripropylamine, etc.

When an active compound of the present invention is basic, salts may be prepared from pharmaceutically acceptable non-toxic acids. Such acids include acetic, benzenesulfonic, benzoic, camphorsulfonic, citric, ethane-sulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Particularly preferred are citric, hydrobromic, maleic, phosphoric, sulfuric, and tartaric acids.

In the discussion of methods of treatment herein, reference to the active compounds is meant to also include the pharmaceutically acceptable salts thereof. While certain formulations are set forth herein, the actual amounts to be administered to the mammal or man in need of same are to be determined by the treating physician.

The invention is further defined by reference to the following examples, which are intended to be illustrative and not limiting.

The following are examples of certain classes. All values unless otherwise specified are in weight percent.

EXAMPLES

Example 1

Biologically Active Peptides Including Peptide Hormones

A. Cyclosporine Lingual Spray

|  | Amounts | preferred amount | most preferred amount |
| --- | --- | --- | --- |
| cyclosporine | 5-50 | 10-35 | 15-25 |
| water | 5-20 | 7.5-50 | 9.5-12 |
| ethanol | 5-60 | 7.5-50 | 10-20 |
| polyethylene glycol | 20-60 | 30-45 | 35-40 |
| flavors | 0.1-5 | 1-4 | 2-3 |

B. Cyclosporine Non-Polar Lingual Spray

|  | Amounts | preferred amount | most preferred amount |
| --- | --- | --- | --- |
| cyclosporine | 1-50 | 3-40 | 5-30 |
| Migylol | 20 | 25 | 30-40 |
| Polyoxyethylated castor oil | 20 | 25 | 30-40 |
| Butane | 25-80 | 30-70 | 33-50 |
| flavors | 0.1-5 | 1-4 | 2-3 |

C. Cyclosporine Non-Polar Bite Capsule

|  | Amounts | preferred amount | most preferred amount |
| --- | --- | --- | --- |
| cyclosporine | 1-35 | 5-25 | 10-20 |
| olive oil | 25-60 | 35-55 | 30-45 |
| polyoxyethylated oleic glycerides | 25-60 | 35-55 | 30-45 |
| flavors | 0.1-5 | 1-4 | 2-3 |

D. Cyclosporine Bite Capsule

|  | Amounts | preferred amount | most preferred amount |
| --- | --- | --- | --- |
| cyclosporine | 5-50 | 10-35 | 15-25 |
| polyethylene glycol | 20-60 | 30-45 | 35-40 |
| glycerin | 5-30 | 7.5-25 | 10-20 |
| propylene glycol | 5-30 | 7.5-25 | 10-20 |
| flavors | 0.1-10 | 1-8 | 3-6 |

E. Sermorelin (as the Acetate) Lingual Spray

|  | Amounts | preferred amount | most preferred |
| --- | --- | --- | --- |
| sermorelin (as the acetate) | .01-5 | .1-3 | .2-1.0 |
| mannitol | 1-25 | 5-20 | 10-15 |
| monobasic sodium phosphate, | 0.1-5 | 1-31 | .5-2.5 |
| dibasic sodium phosphate | 0.01-5 | .05-3 | 0.1-0.5 |
| water |  |  |  |
| ethanol | 5-30 | 7.5-25 | 9.5-15 |
| polyethylene glycol | 20-60 | 30-45 | 35-40 |
| propylene glycol | 5-25 | 10-20 | 12-17 |
| flavors | 0.1-5 | 1-4 | 2-3 |

F. Octreotide Acetate (Sandostatin) Lingual Spray

|  | Amounts | preferred amount | most preferred amount |
| --- | --- | --- | --- |
| octreotide acetate | 0.001-0.5 | 0.005-0.250 | 0.01-0.10 |
| acetic acid | 1-10 | 2-8 | 4-6 |
| sodium acetate | 1-10 | 2-8 | 4-6 |
| sodium chloride | 3-30 | .5-25 | 15-20 |
| flavors | 0.1-5 | 0.5-.4 | 2-3 |
| ethanol | 5-30 | 7.5-20 | 9.5-15 |
| water | 15-95 | 35-90 | 65-85 |
| flavors | 0.1-5 | 1-4 | 2-3 |

G. Calcitonin-Salmon Lingual Spray

|  | Amounts | preferred amount | most preferred amount |
| --- | --- | --- | --- |
| calcitonin-salmon | 0.001-5 | 0.005-2 | 01-1.5 |
| ethanol | 2-15 | 3-10 | 7-9.5 |
| water | 30-95 | 50-90 | 60-80 |
| polyethylene glycol | 2-15 | 3-10 | 7-9.5 |
| sodium chloride | 2.5-20 | 5-15 | 10-12.5 |
| flavors | 0.1-5 | 1-4 | 2-3 |

H. Insulin Lispro, Lingual Spray

|  | Amounts | preferred amount | most preferred amount |
|---|---|---|---|
| insulin | 20-60 | 4-55 | 5-50 |
| glycerin | 0.1-10 | 0.25-5 | 0.1-1.5 |
| dibasic sodium phosphate | 1-15 | 2.5-10 | 4-8 |
| m-cresol, | 1-25 | 5-25 | 7.5-12.5 |
| zinc oxide | 0.01-0.25 | .05-0.15 | 0.075-0.10 |
| m-cresol | 0.1-1 | 0.2-0.8 | 0.4-0.6 |
| phenol | trace amounts | trace amounts | trace amounts |
| ethanol | 5-20 | 7.5-15 | 9-12 |
| water | 30-90 | 40-80 | 50-75 |
| propylene glycol | 5-20 | 7.5-15 | 9-12 |
| flavors | 0.1-5 | 0.5-3 | 0.75-2 | adjust pH to 7.0-7.8 with HCl or NaOH

Example 2

CNS Active Amines and their Salts: Including but not Limited to Tricyclic Amines, GABA Analogues, Thiazides, Phenothiazine Derivatives, Serotonin Antagonists and Serotonin Reuptake Inhibitors

A. Sumatriptan Succinate Lingual Spray

|  | Amounts | preferred amount | most preferred amount |
|---|---|---|---|
| sumatriptan succinate | 0.5-30 | 1-20 | 10-15 |
| ethanol | 5-60 | 7.5-50 | 10-20 |
| propylene glycol | 5-30 | 7.5-20 | 10-15 |
| polyethylene glycol | 0-60 | 30-45 | 35-40 |
| water | 5-30 | 7.5-20 | 10-15 |
| flavors | 0.1-5 | 1-4 | 2-3 |

B. Sumatriptan Succinate Bite Capsule

|  | Amounts | preferred amount | most preferred amount |
|---|---|---|---|
| sumatriptan succinate | 0.01-5 | 0.05-3.5 | 0.075-1.75 |
| polyethylene glycol | 25-70 | 30-60 | 35-50 |
| glycerin | 25-70 | 30-60 | 35-50 |
| flavors | 0.1-10 | 1-8 | 3-6 |

C. Clozepine Lingual Spray

|  | Amounts | preferred amount | most preferred amount |
|---|---|---|---|
| clozepine | 0.5-30 | 1-20 | 10-15 |
| ethanol | 5-60 | 7.5-50 | 10-20 |
| propylene glycol | 5-30 | 7.5-20 | 10-15 |
| polyethylene glycol | 0-60 | 30-45 | 35-40 |
| water | 5-30 | 7.5-20 | 10-15 |
| flavors | 0.1-5 | 1-4 | 2-3 |

D. Clozepine Non-Polar Lingual Spray with Propellant

|  | Amounts | preferred amount | most preferred amount |
|---|---|---|---|
| clozepine | 0.5-30 | 1-20 | 10-15 |
| Migylol | 20-85 | 25-70 | 30-40 |
| Butanol | 5-80 | 30-75 | 60-70 |
| flavors | 0.1-5 | 1-4 | 2-3 |

E. Clozepine Non-Polar Lingual Spray without Propellant

|  | Amounts | preferred amount | most preferred amount |
|---|---|---|---|
| clozepine | 0.5-30 | 1-20 | 10-15 |
| Migylol | 70-99.5 | 80-99 | 85-90 |
| flavors | 0.1-5 | 1-4 | 2-3 |

F. Cyclobenzaprine Non-Polar Lingual Spray

|  | Amounts | preferred amount | most preferred amount |
|---|---|---|---|
| cyclobenzaprine (base) | 0.5-30 | 1-20 | 10-15 |
| Migylol | 20-85 | 25-70 | 30-40 |
| Iso-butane | 15-80 | 30-75 | 60-70 |
| flavors | 0.1-5 | 1-4 | 2-3 |

G. Dexfenfluramine Hydrochloride Lingual Spray

|  | Amounts | preferred amount | most preferred amount |
|---|---|---|---|
| dexfenfluramine Hcl | 5-30 | 7.5-20 | 10-15 |
| ethanol | 5-60 | 7.5-50 | 10-20 |
| propylene glycol | 5-30 | 7.5-20 | 10-15 |
| polyethylene glycol | 0-60 | 30-45 | 35-40 |
| water | 5-30 | 7.5-20 | 10-15 |
| flavors | 0.1-5 | 1-4 | 2-3 |

Example 3

Sulfonylureas

A. Glyburide Lingual Spray

|  | Amounts | preferred amount | most preferred amount |
|---|---|---|---|
| glyburide | 0.25-25 | 0.5-20 | 0.75-15 |
| ethanol | 5-60 | −7.5-50 | 10-20 |
| propylene glycol | 5-30 | 7.5-20 | 10-15 |
| polyethylene glycol | 0-60 | 30-45 | 35-40 |
| water | 2.5-30 | 5-20 | 6-15 |
| flavors | 0.1-5 | 1-4 | 2-3 |

B. Glyburide Non-Polar Bite Capsule

|  | Amounts | preferred amount | most preferred amount |
|---|---|---|---|
| glyburide | 0.01-10 | 0.025-7.5 | 0.1-4 |
| olive oil | 30-60 | 35-55 | 30-50 |
| polyoxyethylated oleic glycerides | 30-60 | 35-55 | 30-50 |
| flavors | 0.1-5 | 1-4 | 2-3 |

Example 4

Antibiotics Anti-Fungals and Anti-Virals

A. Zidovudine [Formerly Called Azidothymidine (AZT) (Retrovir)] Non-Polar Lingual Spray

|  | Amounts | preferred amount | most preferred amount |
|---|---|---|---|
| zidovudine | 10-50 | 15-40 | 25-35 |
| Soya oil | 20-85 | 25-70 | 30-40 |
| Butane | 15-80 | 30-75 | 60-70 |
| flavors | 0.1-5 | 1-4 | 2-3 |

B. Erythromycin Bite Capsule Bite Capsule

|  | Amounts | preferred amount | most preferred amount |
|---|---|---|---|
| erythromycin | 25-65 | 30-50 | 35-45 |
| polyoxyethylene glycol | 5-70 | 30-60 | 45-55 |
| glycerin | 5-20 | 7.5-15 | 10-12.5 |
| flavors | 1-10 | 2-8 | 3-6 |

C. Ciprofloxacin Hydrochloride Bite Capsule

|  | Amounts | preferred amount | most preferred amount |
|---|---|---|---|
| ciprofloxacin hydrochloride | 25-65 | 35-55 | 40-50 |
| glycerin | 5-20 | 7.5-15 | 10-12.5 |
| polyethylene glycol | 120-75 | 30-65 | 40-60 |
| flavors | 1-10 | 2-8 | 3-6 |

D. Zidovudine [Formerly Called Azidothymidine (AZT) (Retrovir)] Lingual Spray

|  | Amounts | preferred amount | most preferred amount |
|---|---|---|---|
| zidovudine | 10-50 | 15-40 | 25-35 |
| water | 30-80 | 40-75 | 45-70 |
| ethanol | 5-20 | 7.5-15 | 9.5-12.5 |
| polyethylene glycol | 5-20 | 7.5-15 | 9.5-12.5 |
| flavors | 0.1-5 | 1-4 | 2-3 |

Example 5

Anti-Emetics

A. Ondansetron Hydrochloride Lingual Spray

|  | Amounts | preferred amount | most preferred amount |
|---|---|---|---|
| ondansetron hydrochloride | 1-25 | 2-20 | 2.5-15 |
| citric acid monohydrate | 1-10 | 2-8 | 2.5-5 |
| sodium citrate dihydrate | 0.5-5 | 1-4 | 1.25-2.5 |
| water | 1-90 | 5-85 | 10-75 |
| ethanol | 5-30 | 7.5-20 | 9.5-15 |
| propylene glycol | 5-30 | 7.5-20 | 9.5-15 |
| polyethylene glycol | 5-30 | 7.5-20 | 9.5-15 |
| flavors | 1-10 | 3-8 | 5-7.5 |

B. Dimenhydrinate Bite Capsule

|  | Amounts | preferred amount | most preferred amount |
|---|---|---|---|
| dimenhydrinate | 0.5-30 | 2-25 | 3-15 |
| glycerin | 5-20 | 7.5-15 | 10-12.5 |
| polyethylene glycol | 45-95 | 50-90 | 55-85 |
| flavors | 1-10 | 2-8 | 3-6 |

C. Dimenhydrinate Polar Lingual Spray

|  | Amounts | preferred amount | most preferred amount |
|---|---|---|---|
| dimenhydrinate | 3-50 | 4-40 | 5-35 |
| water | 5-90 | 10-80 | 15-75 |
| ethanol | 1-80 | 3-50 | 5-10 |
| polyethylene glycol | 1-80 | 3-50 | 5-15 |
| sorbitol | 0.1-5 | 0.2-40 | 0.4-1.0 |
| aspartame | 0.01-0.5 | 0.02-0.4 | 0.04-0.1 |
| flavors | 0.1-5 | 1-4 | 2-3 |

Example 6

Histamine H-2 Receptor Antagonists

A. Cimetidine Hydrochloride Bite Capsule

|  | Amounts | preferred amount | most preferred amount |
|---|---|---|---|
| cimetidine HCl | 10-60 | 15-55 | 25-50 |
| glycerin | 5-20 | 7.5-15 | 10-12.5 |
| polyethylene glycol | 20-90 | 25-85 | 30-75 |
| flavors | 1-10 | 2-8 | 3-6 |

B. Famotidine Lingual Spray

|  | Amounts | preferred amount | most preferred amount |
|---|---|---|---|
| famotidine | 1-35 | 5-30 | 7-20 |
| water | 2.5-25 | 3-20 | 5-10 |
| L-aspartic acid | 0.1-20 | 1-15 | 5-10 |

-continued

|  | Amounts | preferred amount | most preferred amount |
|---|---|---|---|
| polyethylene glycol | 20-97 | 30-95 | 50-85 |
| flavors | 0.1-10 | 1-7.5 | 2-5 |

C. Famotidine Non-Polar Lingual Spray

|  | Amounts | preferred amount | most preferred amount |
|---|---|---|---|
| famotidine | 1-35 | 5-30 | 7-20 |
| Soya oil | 10-50 | 15-40 | 15-20 |
| Butane1 | 5-80 | 30-75 | 45-70 |
| polyoxyethylated oleic glycerides | 10-50 | 15-40 | 15-20 |
| flavors | 0.1-5 | 1-4 | 2-3 |

Example 7

Barbiturates

A. Phenytoin Sodium Lingual Spray

|  | Amounts | preferred amount | most preferred amount |
|---|---|---|---|
| phenytoin sodium | 10-60 | 15-55 | 20-40 |
| water | 2.5-25 | 3-20 | 5-10 |
| ethanol | 5-30 | 7.5-20 | 9.5-15 |
| propylene glycol | 5-30 | 7.5-20 | 9.5-15 |
| polyethylene glycol | 5-30 | 7.5-20 | 9.5-15 |
| flavors | 1-10 | 3-8 | 5-7.5 |

B. Phenytoin Non-Polar Lingual Spray

|  | Amounts | preferred amount | most preferred amount |
|---|---|---|---|
| phenytoin | 5-45 | 10-40 | 15-35 |
| migylol | 10-50 | 15-40 | 15-20 |
| Butane | 15-80 | 30-75 | 60-70 |
| polyoxyethylated oleic glycerides | 10-50 | 15-40 | 15-20 |
| flavors | 0.1-10 | 1-8 | 5-7.5 |

Example 8

Prostaglandins

A. Carboprost Thromethamine Lingual Spray

|  | Amounts | preferred amount | most preferred amount |
|---|---|---|---|
| carboprost thromethamine | 0.05-5 | 0.1-3 | 0.25-2.5 |
| water | 50-95 | 60-80 | 65-75 |
| ethanol | 5-20 | 7.5-15 | 9.5-12.5 |
| polyethylene glycol | 5-20 | 7.5-15 | 9.5-12.5 |
| sodium chloride | 1-20 | 3-15 | 4-8 |
| flavors | 0.1-5 | 1-4 | 2-3 | pH is adjusted with sodium hydroxide and/or hydrochloric acid

B. Carboprost Non-Polar Lingual Spray

|  | Amounts | preferred amount | most preferred amount |
|---|---|---|---|
| carboprost | 0.05-5 | 0.1-3 | 0.25-2.5 |
| migylol | 25-50 | 30-45 | 35-40 |
| Butane | 5-60 | 10-50 | 20-35 |
| polyoxyethylated oleic glycerides | 25-50 | 30-45 | 35-40 |
| flavors | 0.1-10 | 1-8 | 5-7.5 |

Example 9

Neutraceuticals

A. Carnitine as Bite Capsule (Contents are a Paste)

|  | Amounts | preferred amount | most preferred amount |
|---|---|---|---|
| carnitine fumarate | 6-80 | 30-70 | 45-65 |
| soya oil | 7.5-50 | 10-40 | 12.5-35 |
| soya lecithin | 0.001-1.0 | 0.005-0.5 | .01-0.1 |
| Soya fats | 7.5-50 | 10-40 | 12.5-35 |
| flavors | 1-10 | 2-8 | 3-6 |

B. Valerian as Lingual Spray

|  | Amounts | preferred amount | most preferred amount |
|---|---|---|---|
| valerian extract | 0.1-10 | 0.2-7 | 0.25-5 |
| water | 50-95 | 60-80 | 65-75 |
| ethanol | 5-20 | 7.5-15 | 9.5-12.5 |
| polyethylene glycol | 5-20 | 7.5-15 | 9.5-12.5 |
| flavors | 1-10 | 2-8 | 3-6 |

C. Echinacea as Bite Capsule

|  | Amounts | preferred amount | most preferred amount |
|---|---|---|---|
| echinacea extract | 30-85 | 40-75 | 45-55 |
| soya oil | 7.5-50 | 10-40 | 12.5-35 |
| soya lecithin | 0.001-1.0 | 0.005-0.5 | .01-0.1 |
| Soya fats | 7.5-50 | 10-40 | 12.5-35 |
| flavors | 1-10 | 2-8 | 3-6 |

D. Mixtures of Ingredients

|  | Amounts | preferred amount | most preferred amount |
|---|---|---|---|
| magnesium oxide | 15-40 | 20-35 | 25-30 |
| chromium picolinate | 0.01-1.0 | 0.02-0.5 | .025-0.75 |
| folic acid | .025-3.0 | 0.05-2.0 | 0.25-0.5 |
| vitamin B-12 | 0.01-1.0 | 0.02-0.5 | .025-0.75 |
| vitamin E | 15-40 | 20-35 | 25-30 |
| Soya oil | 10-40 | 12.5-35 | 15-20 |
| soya lecithin | 0.1-5 | 0.2-4 | 0.5-1.5 |
| soya fat | 10-40 | 15-35 | 17.5-20 |

Example 10

Sleep Inducers (also CNS active amine)

A. Diphenhydramine Hydrochloride Lingual Spray

|  | Amounts | preferred amount | most preferred amount |
|---|---|---|---|
| diphenhydramine HCl | 3-50. | 4-40 | 5-35 |
| water | 5-90 | 10-80 | 50-75 |
| ethanol | 1-80 | 3-50 | 5-10 |
| polyethylene glycol | 1-80 | 3-50 | 5-15 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |

Example 11

Anti-Asthmatics-Bronchodilators

A. Isoproterenol Hydrochloride as Polar Lingual Spray

|  | Amounts | preferred amount | most preferred amount |
|---|---|---|---|
| isoproterenol Hydrochloride | 0.1-10 | 0.2-7.5 | 0.5-6 |
| water | 5-90 | 10-80 | 50-75 |
| ethanol | 1-80 | 3-50 | 5-10 |
| polyethylene glycol | 1-80 | 3-50 | 5-15 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |

B. Terbutaline Sulfate as Polar Lingual Spray

|  | Amounts | preferred amount | most preferred amount |
|---|---|---|---|
| terbutaline sulfate | 0.1-10 | 0.2-7.5 | 0.5-6 |
| water | 5-90 | 10-80 | 50-75 |
| ethanol | 1-10 | 2-8 | 2.5-5 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |

C. Terbutaline as Non-Polar Lingual Spray

|  | Amounts | preferred amount | most preferred amount |
|---|---|---|---|
| terbutaline | 0.1-10 | 0.2-7.5 | 0.5-6 |
| migylol | 25-50 | 30-45 | 35-40 |
| isobutane | 5-60 | 10-50 | 20-35 |
| polyoxyethylated oleic glycerides | 25-50 | 30-45 | 35-40 |
| flavors | 0.1-10 | 1-8 | 5-7.5 |

D. Theophylline Polar Bite Capsule

|  | Amounts | preferred amount | most preferred amount |
|---|---|---|---|
| theophylline | 5-50 | 10-40 | 15-30 |
| polyethylene glycol | 20-60 | 25-50 | 30-40 |
| glycerin | 25-50 | 35-45 | 30-40 |
| propylene glycol | 25-50 | 35-45 | 30-40 |
| flavors | 0.1-5 | 1-4 | 2-3 |

E. Albuterol Sulfate as Polar Lingual Spray

|  | Amounts | preferred amount | most preferred amount |
|---|---|---|---|
| albuterol sulfate | 0.1-10 | 0.2-7.5 | 0.5-6 |
| water | 5-90 | 10-80 | 50-75 |
| ethanol | 1-10 | 2-8 | 2.5-5 |
| Sorbitol | 0.1-5 | 0.2-4 | 0.4-1.0 |
| aspartame | 0.01-0.5 | 0.02-0.4 | 0.04-0.1 |
| flavors | 0.1-5 | 1-4 | 2-3 |

Example 12

Polar Solvent Formulations Using a Propellant

A. Sulfonylurea

|  | Amount | Preferred Amount | Most-Preferred Amount |
|---|---|---|---|
| glyburide | 0.1-25% | 0.5-15% | 0.6-10% |
| Ethanol | 40-99% | 60-97% | 70-97% |
| Water | 0.01-5% | 0.1-4% | 0.2-2% |
| Flavors | 0.05-10% | 0.1-5% | 0.1-2.5% |
| Propellant | 2-10% | 3-5% | 3-4% |

B. Prostaglandin E (Vasodilator)

|  | Amount | Preferred Amount | Most-Preferred Amount |
|---|---|---|---|
| prostaglandin $E_1$ | 0.01-10% | 0.1-5% | 0.2-3% |
| Ethanol | 10-90% | 20-75% | 25-50% |
| Propylene glycol | 1-90% | 5-80% | 10-75% |
| Water | 0.01-5% | 0.1-4% | 0.2-2% |
| Flavors | 0.05-10% | 0.1-5% | 0.1-2.5% |
| Propellant | 2-10% | 3-5% | 3-4% |

C. Promethazine (Antiemetic, Sleep Inducer, and CNS Active Amine)

|  | Amount | Preferred Amount | Most-Preferred Amount |
|---|---|---|---|
| promethazine | 1-25% | 3-15% | 5-12% |
| Ethanol | 10-90% | 20-75% | 25-50% |
| Propylene glycol | 1-90% | 5-80% | 10-75% |
| Water | 0.01-5% | 0.1-4% | 0.2-2% |
| Flavors | 0.05-10% | 0.1-5% | 0.1-2.5% |
| Propellant | 2-10% | 3-5% | 3-4% |

D. Meclizine

|  | Amount | Preferred Amount | Most-Preferred Amount |
|---|---|---|---|
| meclizine | 1-25% | 3-15% | 5-12% |
| Ethanol | 1-15% | 2-10% | 3-6 |
| Propylene glycol | 20-98% | 5-90% | 10-85% |
| Water | 0.01-5% | 0.1-4% | 0.2-2% |
| Flavors | 0.05-10% | 0.1-5% | 0.1-2.5% |
| Propellant | 2-10% | 3-5% | 3-4% |

Example 13

Zolpidem Formulations

A. A propellant free zolpidem formulation containing a polar solvent has the following formula:

| Component | Percent (w/w) |
|---|---|
| Zolpidem tartrate | 2.5 |
| Propylene glycol | 15 |
| Glycerol | 10 |
| Bitter mask | 0.2 |
| Benzalkonium chloride | 0.1 |
| Citrate buffer (1N, pH 6) | 8 |
| Ethanol | QS 100 |

B. A zolpidem formulation in a polar solvent with a propellant has the following formula:

| Component | Percent (w/w) |
|---|---|
| Zolpidem tartrate | 2.5 |
| Ethanol | 35 |
| Glycerol | 10 |
| Bitter mask | 0.2 |
| Butane | QS 100 |

C. A propellant free zolpidem formulation in a mixture of a polar and a non-polar solvent has the following formula:

| Component | Percent (w/w) |
|---|---|
| Zolpidem tartrate | 0.5 |
| MIGLYOL ® | 15 |
| Lemon oil | 10 |
| Ethanol | QS to 100 |

D. A zolpidem formulation in a mixture of a polar solvent and a non-polar solvent with a propellant can be made according to the following formula:

| Component | Percent (w/w) |
|---|---|
| Zolpidem tartrate | 0.5 |
| Liquid paraffin | 15 |
| Lemon oil | 10 |
| Ethanol | 40 |
| Butane | QS 100 |

E. A propellant free zolpidem formulation in a non-polar solvent can be made according to the following formula:

| Component | Percent (w/w) |
|---|---|
| Zolpidem tartrate | 0.2 |
| Lemon oil | 0.1 |
| MIGLYOL ® | Qs to 100 |

F. A zolpidem formulation in a non-polar solvent with a propellant can be made according to the following formula:

| Component | Percent (w/w) |
|---|---|
| Zolpidem tartrate | 0.2 |
| Lemon oil | 0.1 |
| MIGLYOL ® | 50 |
| Butane | Qs to 100 |

What is claimed is:

1. A method of treating insomnia in a human patient, comprising:
providing an oral spray composition comprising zolpidem or a pharmaceutically acceptable salt thereof in an amount of between 2.5 and 20 percent by weight of the total composition;
a polar solvent in an amount between 15 and 60 percent by weight of the total composition; and
water; and
spraying the composition on the oral mucosa of the patient to provide transmucosal absorption of an amount of zolpidem through the oral mucosa to the systemic circulatory system of the patient sufficient to treat the patient's insomnia.

2. The method of claim 1, wherein the composition further comprises a taste mask and/or flavoring agent in an amount of between 0.1 and 10 percent by weight of the total composition.

3. The method of claim 1, wherein the zolpidem or a pharmaceutically acceptable salt thereof is present in an amount between 2.5 and 15 percent by weight of the total composition.

4. The method of claim 1, wherein the zolpidem or a pharmaceutically acceptable salt thereof is present in an amount between 2.5 and 10 percent by weight of the total composition.

5. The method of claim 1, wherein the pharmaceutically acceptable salt thereof is zolpidem tartrate.

6. The method of claim 1, wherein the polar solvent is present in an amount between 25 and 50 percent by weight of the total composition.

7. The method of claim 1, wherein the polar solvent is present in an amount between 30 and 45 percent by weight of the total composition.

8. The method of claim 1, wherein the polar solvent is selected from the group consisting of polyethylene glycols having a molecular weight between 400 and 1000, $C_2$ to $C_8$ mono- and poly-alcohols, and $C_7$ to $C_{18}$ alcohols of linear or branched configuration.

9. The method of claim 1, wherein the polar solvent is polyethylene glycol.

10. The method of claim 1, wherein the polar solvent is ethanol.

11. The method of claim 1, wherein the polar solvent is propylene glycol.

12. The method of claim 1, wherein the composition comprises a flavoring agent selected from the group consisting of synthetic or natural oil of peppermint, oil of spearmint, citrus oil, fruit flavors, sweeteners, and mixtures thereof.

13. The method of claim 1, wherein the amount of the spray is predetermined.

14. The method of claim 1, wherein the composition is propellant free.

15. The method of claim 1, wherein the composition further comprises a buffer.

16. The method of claim 1, wherein the composition comprises zolpidem tartrate and propylene glycol.

17. The method of claim 16, wherein the zolpidem tartrate is present in an amount between 2.5 and 10 percent by weight of the total composition.

18. The method of claim 17, wherein the propylene glycol is present in an amount between 20 and 45 percent by weight of the total composition.

19. The method of claim 18, further comprising a buffer.

20. The method of claim 19, further comprising a flavorant or taste masking agent.

21. The method of claim 20, wherein the composition is propellant free.

\* \* \* \* \*

UNITED STATES PATENT AND TRADEMARK OFFICE
CERTIFICATE OF CORRECTION

| | | |
|---|---|---|
| PATENT NO. | : 7,632,517 B2 | |
| APPLICATION NO. | : 10/671715 | |
| DATED | : December 15, 2009 | |
| INVENTOR(S) | : Dugger, III et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this

Second Day of November, 2010

David J. Kappos
*Director of the United States Patent and Trademark Office*